United States Patent
Millard et al.

(10) Patent No.: US 10,004,392 B2
(45) Date of Patent: *Jun. 26, 2018

(54) DEVICE AND METHOD FOR CONDUCTING A PAP SMEAR TEST

(71) Applicants: Matthew D. Millard, La Jolla, CA (US); Imran Jawaid, Hollywood, CA (US); Winston L. Alexis, Plantation, FL (US)

(72) Inventors: Matthew D. Millard, La Jolla, CA (US); Imran Jawaid, Hollywood, CA (US); Winston L. Alexis, Plantation, FL (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/201,687

(22) Filed: Jul. 5, 2016

(65) Prior Publication Data

US 2017/0119240 A1    May 4, 2017

Related U.S. Application Data (63) Continuation-in-part of application No. 14/145,764, filed on Dec. 31, 2013, now Pat. No. 9,381,002.

(51) Int. Cl.
*A61B 1/31* (2006.01)
*A61B 1/303* (2006.01)
(Continued)

(52) U.S. Cl.
CPC .......... *A61B 1/303* (2013.01); *A61B 1/00142* (2013.01); *A61B 1/018* (2013.01); *A61B 1/05* (2013.01); *A61B 1/0684* (2013.01); *A61B 10/04* (2013.01); *A61B 34/20* (2016.02); *A61B 2010/0216* (2013.01); *A61B 2034/2057* (2016.02); *A61B 2090/373* (2016.02)

(58) Field of Classification Search
CPC . A61B 10/04; A61B 19/5244; A61B 1/00142; A61B 1/018; A61B 1/05; A61B 1/0684; A61B 1/303; A61B 2010/0216; A61B 2019/5231; A61B 2019/5257
See application file for complete search history.

(56) References Cited

U.S. PATENT DOCUMENTS

2006/0052662 A1*  3/2006  Kress ............... A61B 1/0008
                                                    600/123
2007/0213590 A1*  9/2007  Squicciarini ....... A61B 1/00087
                                                    600/172
(Continued)

*Primary Examiner* — Mark Remaly
(74) *Attorney, Agent, or Firm* — John R. Ross; John R. Ross, III (57) ABSTRACT

A protective guide for protecting a cell extraction device during a Pap smear. A camera protective cover encloses a camera and a light emitting device. A thin, flexible transparent sheath encloses the camera cover. A cell extraction device cover encloses the cell extraction device. The location of the cervix is determined by utilizing the camera. The cell extraction device is pushed outward from the cell extraction device cover so that said cell extraction device head contacts the cervix and removes cells from the cervix. The cell extraction device is pulled back into the cell extraction device cover after the cells have been removed from the cervix. In a preferred embodiment the camera and light emitting device is an endoscope and the camera cover is an endoscope cover.

18 Claims, 12 Drawing Sheets

(51) Int. Cl.
*A61B 1/018* (2006.01)
*A61B 1/00* (2006.01)
*A61B 10/04* (2006.01)
*A61B 1/05* (2006.01)
*A61B 1/06* (2006.01)
*A61B 34/20* (2016.01)
*A61B 10/02* (2006.01)
*A61B 90/00* (2016.01)

(56) References Cited

U.S. PATENT DOCUMENTS

2012/0232408 A1* 9/2012 Weller-Brophy .. A61B 1/00165
600/478
2013/0267870 A1* 10/2013 Lonky ................ A61B 10/02
600/569

* cited by examiner

FIG. 21

FIG. 23

DEVICE AND METHOD FOR CONDUCTING A PAP SMEAR TEST

The present invention relates to medical devices and procedures, and in particular, to medical devices and procedures for conducting a Pap smear test. This application is a continuation-in-part (CIP) of U.S. patent application Ser. No. 14/145,764, filed Dec. 31, 2013, soon to issue as U.S. Pat. No. 9,381,002 on Jul. 5, 2016, all of which is incorporated herein by reference.

BACKGROUND OF THE INVENTION

The Papanicolaou test (also called Pap smear, Pap test, cervical smear, or smear test) is a screening test used to detect potentially pre-cancerous and cancerous processes in the endocervical canal (transformation zone) of the female reproductive system.

A Pap smear is accomplished by usage of a cell extraction device such as a Pap smear spatula and Pap smear brush or alternatively by utilization of a Pap smear broom. In either case, the medical practitioner begins by inserting a speculum into the woman's vagina, which spreads the vagina open and allows access to the cervix. If using the spatula and brush, the medical practitioner then collects a sample of cells from the outer opening of the cervix by scraping it with the spatula. Then, an endocervical brush is rotated in the central opening of the cervix. Alternatively the medical practitioner may opt to use a plastic-fronded broom (Pap smear broom) in place of the spatula and brush. The cells are removed from the patient and are placed on a glass slide that is sent to a laboratory to be checked for abnormalities.

Speculum Problems

As stated above, the prior art method of conducting a Pap smear involves the use of a speculum to spread open the vagina. The utilization of the speculum can be extremely uncomfortable and painful to many women as the vagina is spread apart. Some women have even described the speculum as agonizing. The fear and apprehension associated with the speculum has unfortunately caused many women to delay the Pap smear test or, in some cases, to even avoid it entirely. This is unacceptable because it can allow preventable cancer to remain undiagnosed.

Endoscopes

Endoscopes are well known. The endoscope is a medical instrument for viewing the interior of the body and is used for diagnostic examinations and surgical procedures. The endoscope typically includes a USB endoscope camera, light emitting diodes (usually 4 LEDs) and a USB connection. The wide spread use of endoscopes can be attributed to their ease of use, in particular, how simple and inexpensive it is to connect the endoscope camera to a large screen, typically by a USB connection or a video cable. Additionally, LED's illuminate surfaces or spaces that would otherwise need to be surgically opened or enlarged to viewing width.

What is needed is a better device and method for conducting a Pap smear. Furthermore, a data base compiled of patient information from a regular medical examination would be indispensable to the field of medicine.

SUMMARY OF THE INVENTION

The present invention provides a protective guide for protecting a cell extraction device during a Pap smear. A camera protective cover encloses a camera and a light emitting device. A thin, flexible transparent sheath encloses the camera cover. A cell extraction device cover encloses the cell extraction device. The location of the cervix is determined by utilizing the camera. The cell extraction device is pushed outward from the cell extraction device cover so that said cell extraction device head contacts the cervix and removes cells from the cervix. The cell extraction device is pulled back into the cell extraction device cover after the cells have been removed from the cervix. In a preferred embodiment the camera and light emitting device is an endoscope and the camera cover is an endoscope cover.

BRIEF DESCRIPTION OF THE DRAWINGS

FIGS. 5A-8B show the utilization of a preferred embodiment of the present invention.

DETAILED DESCRIPTION OF THE PREFERRED EMBODIMENTS

Protective guide 1 (FIG. 1) allows for a more comfortable, more efficient Pap smear in that a Pap smear can now be conducted without the utilization of a speculum. The patient no longer has to experience the fear, pain and apprehension commonly associated with a Pap smear. Protective guide 1 is very practical and low cost. It allows for very efficient and comfortable Pap smears.

Figure 1:
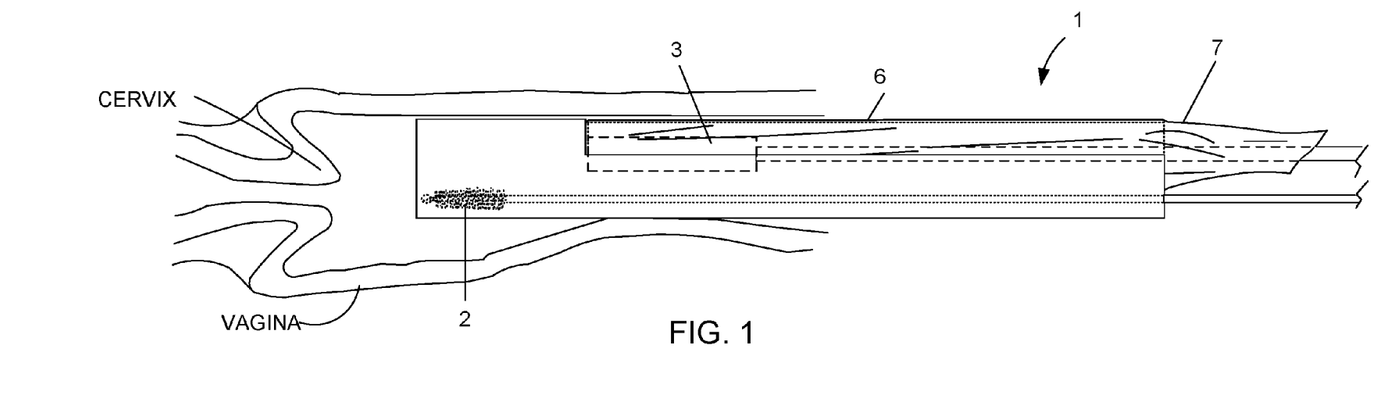
FIGS. 1 and 2 show the utilization of a preferred embodiment of the present invention.
Figure 2:
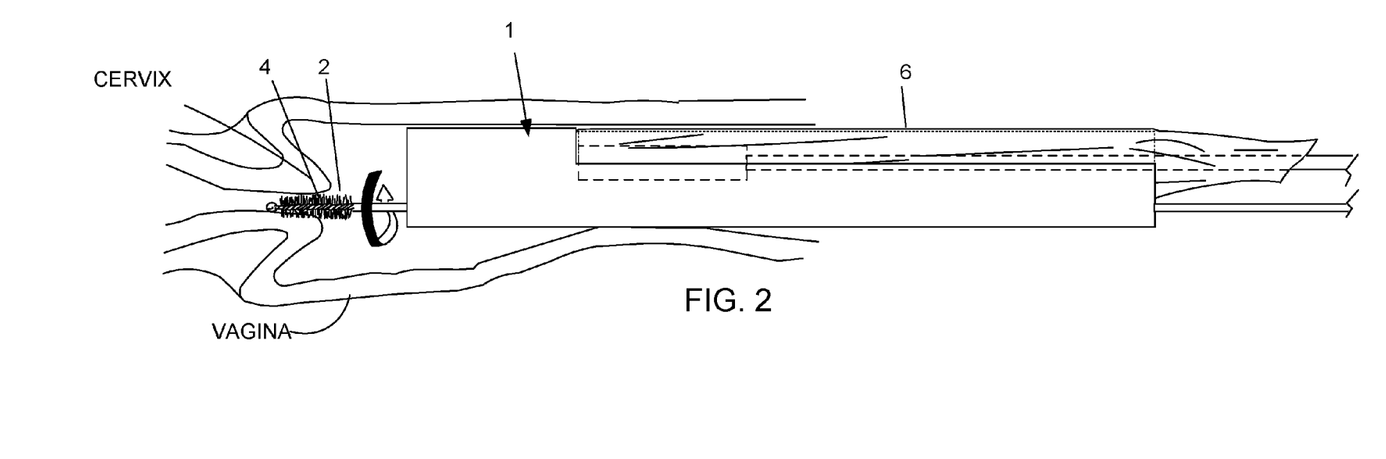

FIGS. 1 and 2 show preferred Pap smear brush 2 and endoscope 3 protected by protective guide 1. Protective guide 1 is inserted into the vagina of a patient. Pap smear brush 2 is contained within protective guide 1. Endoscope 3 is enclosed within endoscope cover 6 of protective guide 1. Thin, flexible transparent latex cover 7 is wrapped around endoscope cover 5. In one preferred embodiment cover 7 is a condom.

In FIG. 1, the medical examiner has located the cervix by utilization of endoscope 3. In FIG. 2, the medical examiner has pushed Pap smear brush 2 outward so that brush head 4 is in contact with the cervix and surrounding tissue. The medical examiner is able to remove cells from the cervix for examination as shown. After the medical examiner has removed the cells from the cervix, he will retract the Pap smear brush back inside protective guide 1 so that it is in the position shown in FIG. 1. Protective guide 1 can then be withdrawn from the vagina.

Preferred Protective Guide

Figures 3, 4A, 4B, 4C, 4D, 4E, 4F, 4G, 4H:
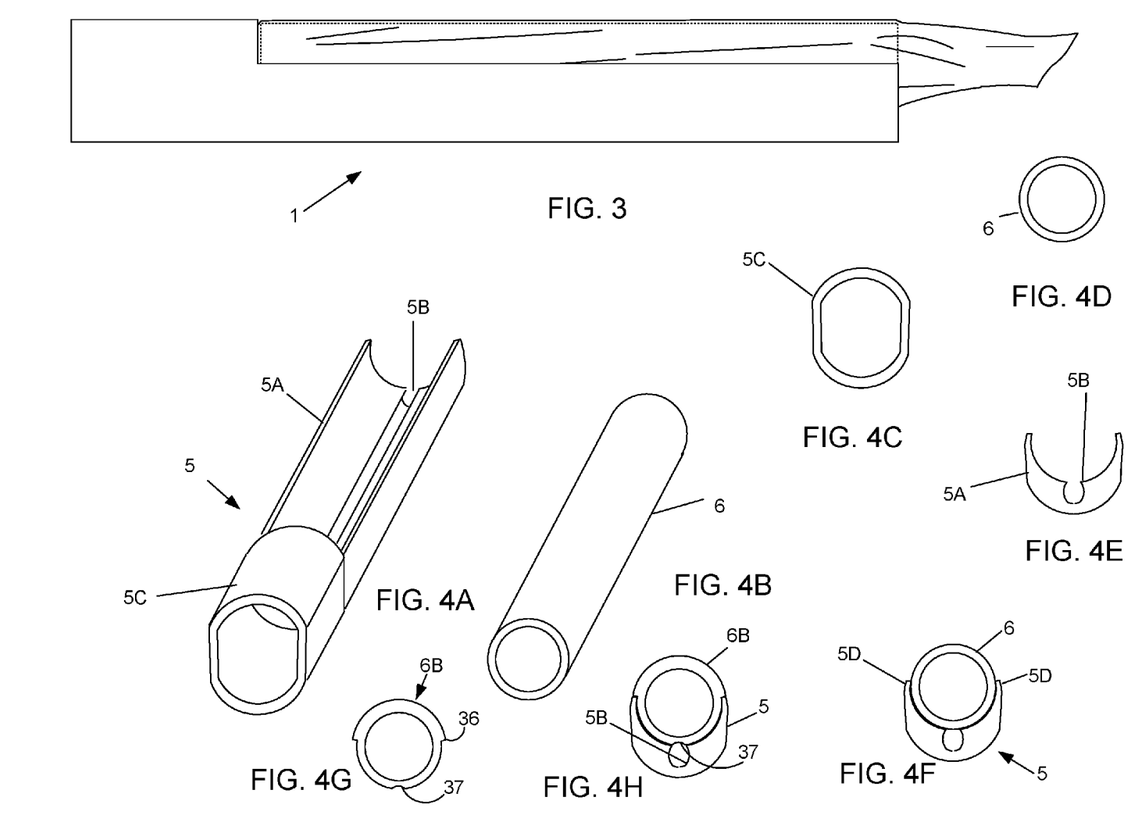
FIG. 3 shows a side view of a preferred protective guide.
FIG. 4A-4H show views of a preferred brush cover and a preferred endoscope cover

FIG. 3 shows a side view of a preferred protective guide 1. FIG. 4B shows a perspective view of endoscope cover 6 and FIG. 4A shows a perspective view of brush cover 5. Endoscope cover 6 is hollow and tubular. Brush cover 5 includes attachment section 5A, brush channel 5B, and front compartment 5C (see also FIGS. 4C-4F). Brush cover 5 preferably includes upper rails 5D which function to allow a secure press-fit with endoscope cover 6.

Protective guide 1 is preferably plastic and is preferably fabricated utilizing an injection molding process for a smooth texture. Brush channel 5B provides a tunnel that extends through protective guide 1 to allow access and movement for the Pap smear brush 2. When the Pap smear brush 2 is fully inserted inside brush channel 2 of protective guide 1, the brush head will be contained within the brush channel and covered by brush cover 5 and endoscope cover 6.

Utilization of a Preferred Protective Guide

Figure 5A:
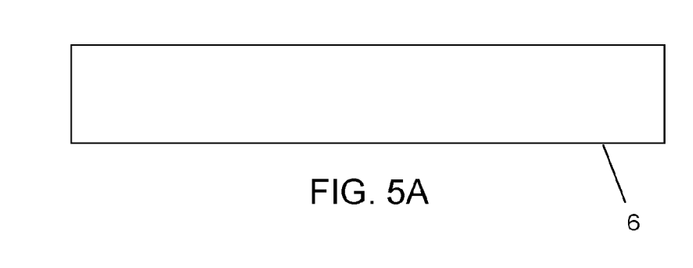
Figure 5B:
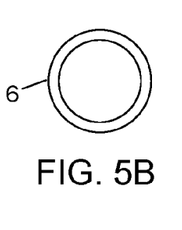
Figure 5C:
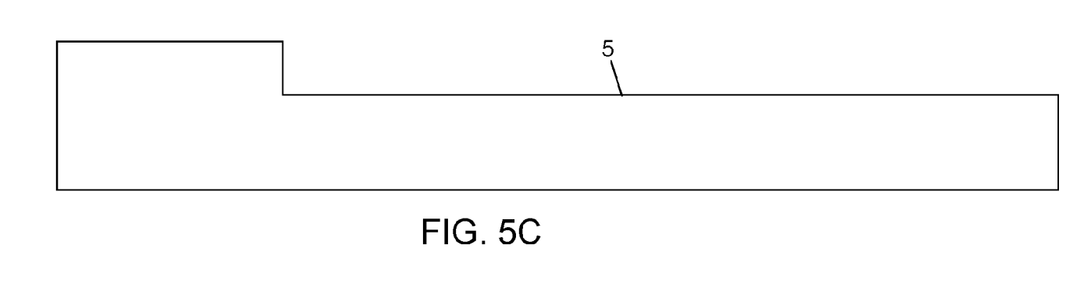
Figure 5D:
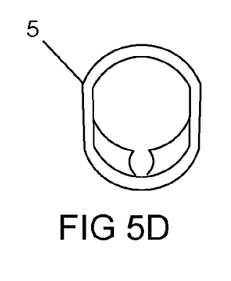

FIG. 5A shows a side view and FIG. 5B shows a front view of endoscope cover 6. FIG. 5C shows a side view and FIG. 5D shows a front view of brush cover 5.

Figure 6:
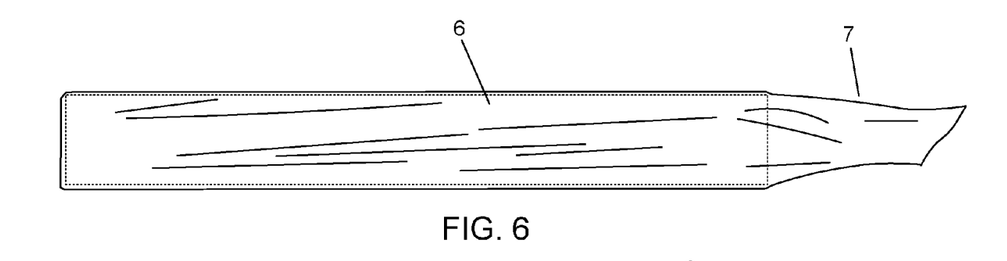

In FIG. 6 the user has placed endoscope cover 6 inside thin, transparent latex cover 7. Latex cover 7 functions as a sheath and as a protective barrier. It covers and protects the endoscope and a portion of the endoscope cord as well as providing for a more comfortable insertion of protective guide 1 into the vagina. It also prevents germs and bacteria that may be present on the endoscope or that may be present on the endoscope cord from coming in contact with the patient. Latex cover 7 is transparent and allows for unobstructed viewing via the endoscope camera.

Figures 7A, 7B:
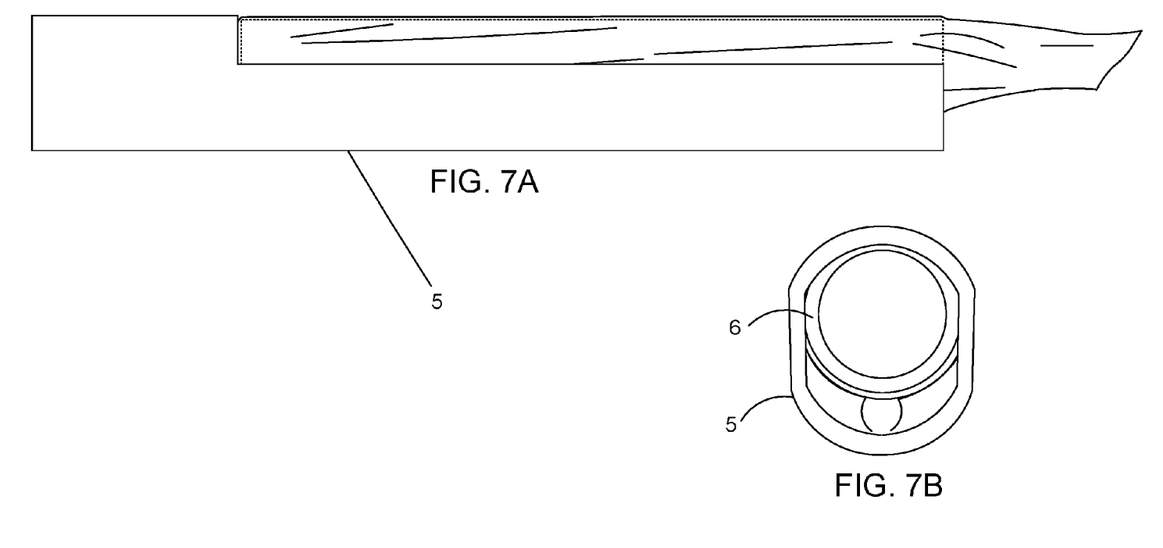

In FIGS. 7A and 7B the user has press fit endoscope cover 6 into brush cover 5 so that brush cover 5 is held in place by friction force.

Figure 8A:
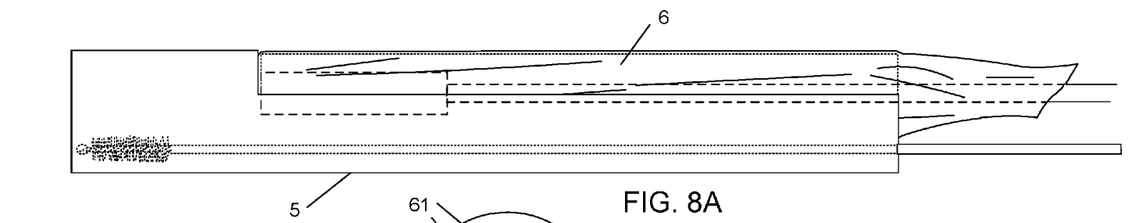
Figure 8B:
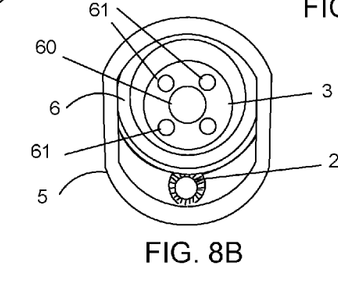

In FIGS. 8A-8B the user has inserted endoscope 3 into endoscope cover 6 and he has inserted Pap smear brush 2 into brush cover 5. FIG. 8B shows a front view of endoscope 3 with camera 60 and light emitting diodes (LEDS) 61. Protective guide 1 is now ready for insertion into the patient's vagina.

Figure 9:
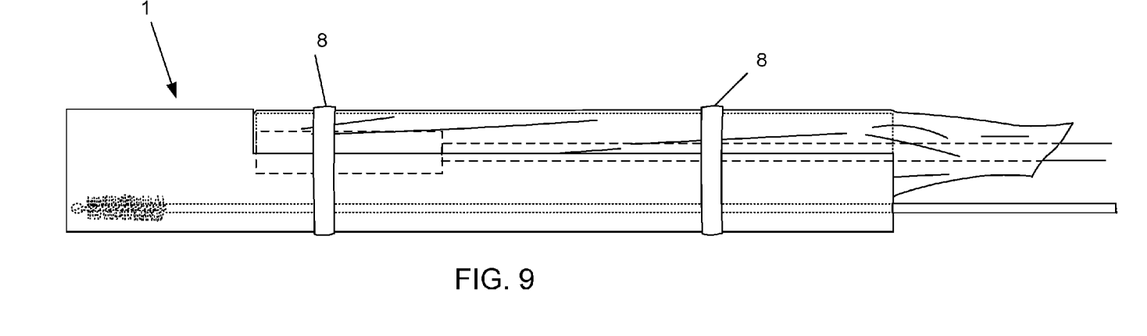
FIG. 9 shows another preferred embodiment of the present invention.

FIG. 9 shows an optional embodiment in which bands 8 have been wrapped around protective guide 1. Bands 8 provide reinforcement to the press fit between endoscope cover 6 and brush cover 5.

In FIG. 1 protective guide 1 has been inserted into the patient's vagina. The image provided by endoscope 3 is providing the medical examiner with a good image of the cervix.

In FIG. 2, the medical examiner has pushed brush 2 outward so that broom head 10 is able to contact the cervix. The bristles of brush head 4 are inserted into the endocervical canal so that they are able to fully contact the ectocervix. The medical examiner preferably pushes gently, and rotates brush section 10 in a clockwise direction five times. After completion the medical examiner may retract brush head back into protective guide 1 and then remove protective guide 1 from the vagina.

Other Embodiments

Figure 10:
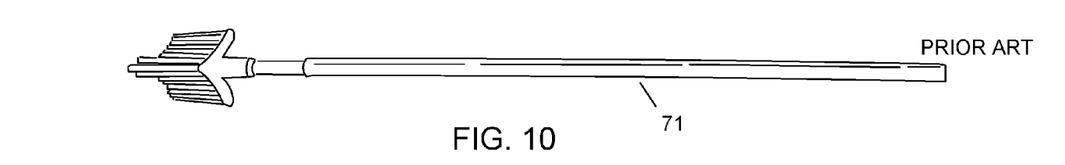
FIG. 10 shows a prior art Pap smear broom.
Figure 11:
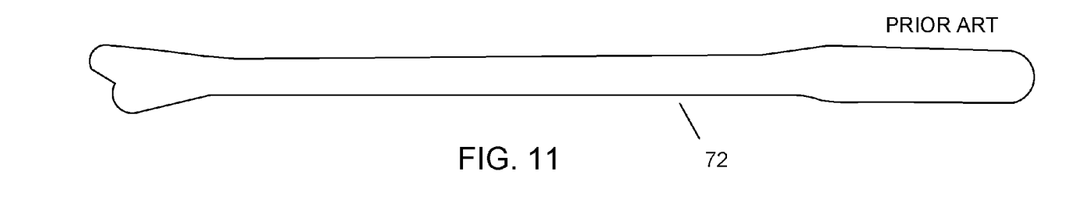
FIG. 11 shows a prior art Pap smear spatula.

Other embodiments of the present invention may also be utilized. For example, brush 2 may be replaced with Pap smear broom 71 (FIG. 10) or Pap smear spatula 72 (FIG. 11).

Figure 12:
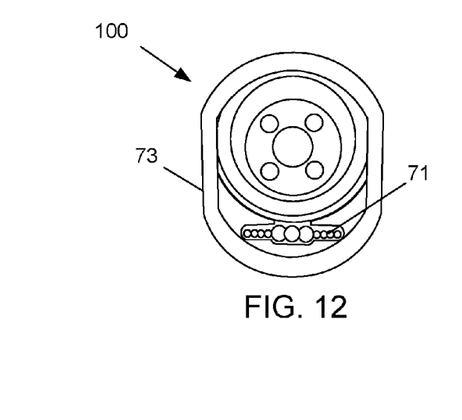
FIG. 12 shows another preferred embodiment of the present invention.

FIG. 12 shows protective guide 100 utilizing Pap smear broom 71 and broom cover 73.

Figure 13:
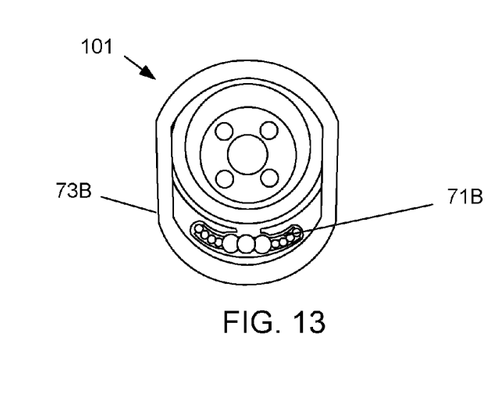
FIG. 13 shows another preferred embodiment of the present invention.

FIG. 13 shows protective guide 101 utilizing Pap smear broom 71B and broom cover 73B. Pap smear broom 71B is contoured so that it follows the curvature of broom cover 73B. This allows for the head of broom 71B to made with greater surface area.

Also, FIGS. 4G and 4H show a preferred endoscope cover 6B. Endoscope cover 6B includes lip 36 and dimple 37. Lip 36 allows for a smoother fit when endoscope cover 6B is press fit onto brush cover 5. This increases comfort for the patient. Also dimple 37 corresponds with brush channel 5B of brush cover 5 for a better fit for Pap smear brush 2.

Figure 14:
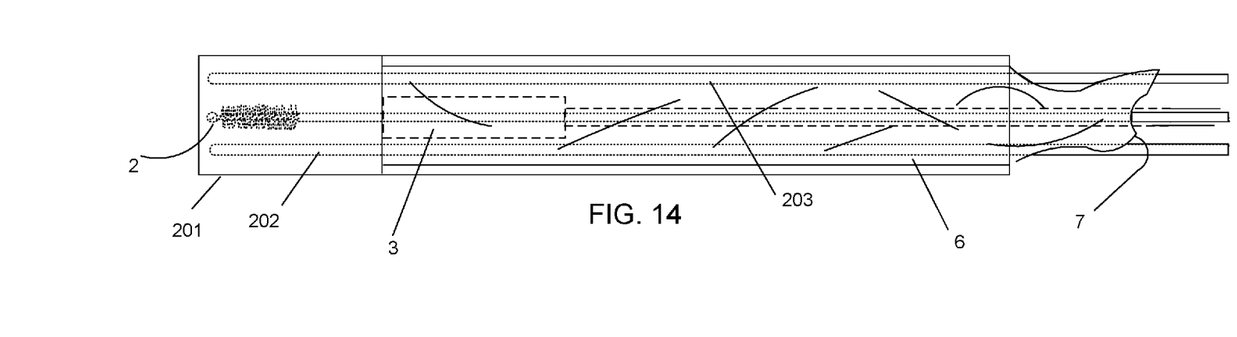
FIGS. 14-16 show another preferred embodiment of the present invention.
Figure 15:
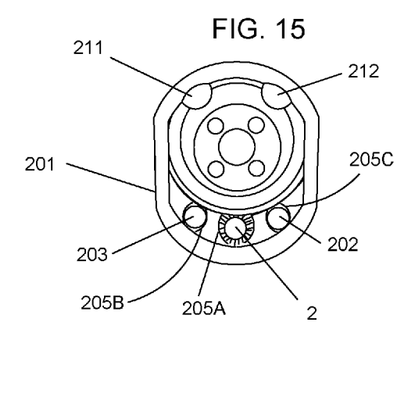
Figure 16:
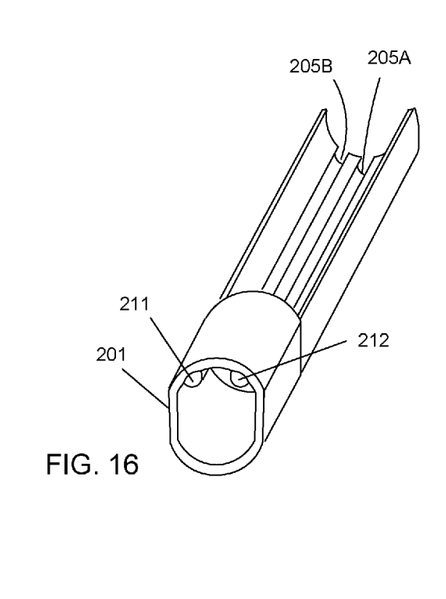

FIGS. 14-16 show another preferred embodiment of the present invention. Brush cover 201 includes temperature probe channel 205B, brush channel 205A and pH probe channel 205C. Temperature probe 203 is inserted as shown into temperature probe channel 205B. Pap smear brush 2 is inserted into brush channel 205A and pH probe 202 is inserted into pH probe channel 205C. Lights 211 and 212 are mounted onto brush cover 201 as shown. As with the earlier preferred embodiments, endoscope 3 is contained within endoscope cover 6. Latex cover 7 covers endoscope cover 6. Endoscope cover 6 is press fit onto brush cover 201.

pH Probe

PH probe 202 is hand controllable by the user in a fashion similar to pap smear brush 2. PH probe 202 may be extended outward from brush cover 201 to make contact within the vagina to determine the hydrogen concentration of the vagina in different places. In this fashion, the pH reading can be determined during a regular screening event with a patient. The user will be able to accurately control pH probe 202 by utilization of the camera in endoscope 3.

Temperature Probe

Figure 23:
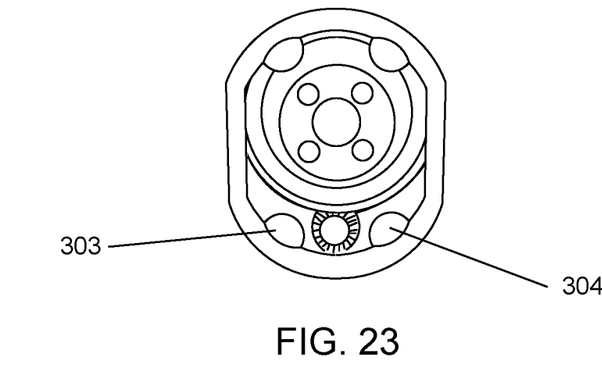

Temperature probe 203 is hand controllable by the user in a fashion similar to pap smear brush 2. Temperature probe 203 may be extended outward from brush cover 201 to make contact within the vagina so as to determine the temperature of the vagina in different places. In this fashion, the temperature reading can be determined during a regular screening event with a patient. The user will be able to accurately control temperature probe 203 by utilization of the camera in endoscope 3. In a preferred embodiment, temperature probe 203 is a thermocouple. Alternatively, as shown in FIG. 23, temperature probe 303 can also be permanently fixed in place to determine the temperature throughout the screening process at different points in the vagina.

Data Mining

Data collected from pap smear brush 2, pH probe 202 and temperature probe 203 is preferably saved onto a computer database. This data may be used as appropriate to keep a record for a patient's health progress. Additionally, data from multiple patients may be compiled and shared to help improve health and treat disease as appropriate.

Additional Lights

As shown in FIGS. 15 and 16, lights 211 and 212 are rigidly mounted onto brush cover 201. The additional lights may be used to provide better lighting within the vagina for the benefit of endoscope 3. Also, by adjusting the light intensity and wavelengths, it is possible to treat medical complications and diseases with light. Additionally lights 211 and 212 may be used to conduct therapy.

Fluid Delivery Tube

Figure 17:
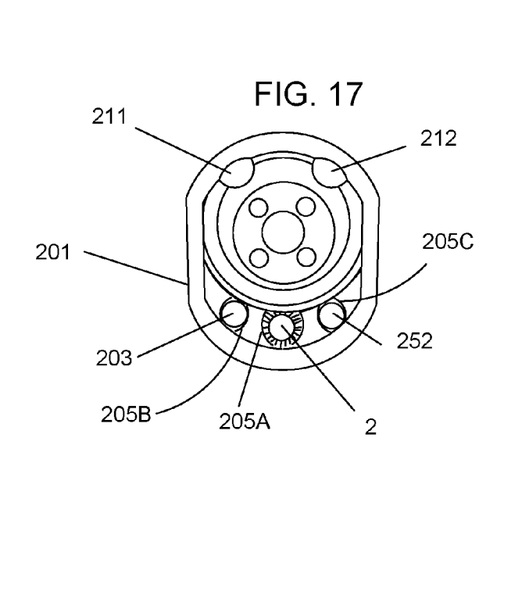
FIGS. 17-18 show another preferred embodiment of the present invention.
Figure 18:
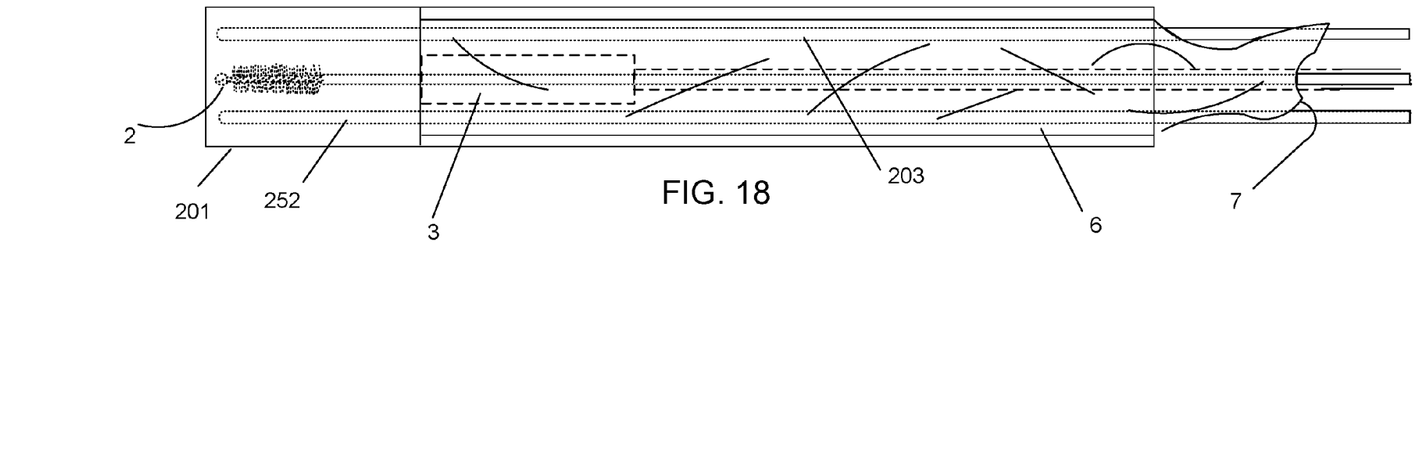

FIGS. 17 and 18 show the utilization of fluid delivery tube 252. Fluid delivery tube 252 is hand controllable by the user in a fashion similar to pap smear brush 2. Fluid delivery tube 252 may be extended outward from brush cover 201 to make contact within the vagina so as to so as to be able to deliver fluid into the vagina in very specific locations. The type of fluid delivered can be modified based on the needs of the patient. Some fluid types are acetic acid, a base, dye or a liquid medication. The user will be able to accurately control fluid delivery tube 252 by utilization of the camera in endoscope 3. In a preferred embodiment, fluid delivery tube 252 is connected to a syringe or a fluid pump. Alternatively, delivery tube 304 (FIG. 23) can also be rigidly fixed in place and used to deliver fluid to a larger area, if desirable.

Expanding the Vaginal Canal

Figure 19:
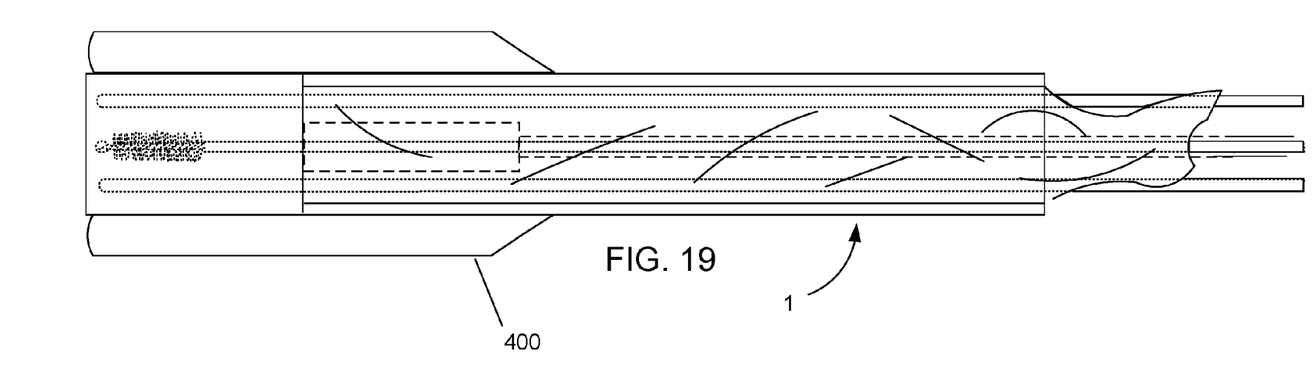
FIGS. 19-23 show other preferred embodiments of the present invention.
Figure 20:
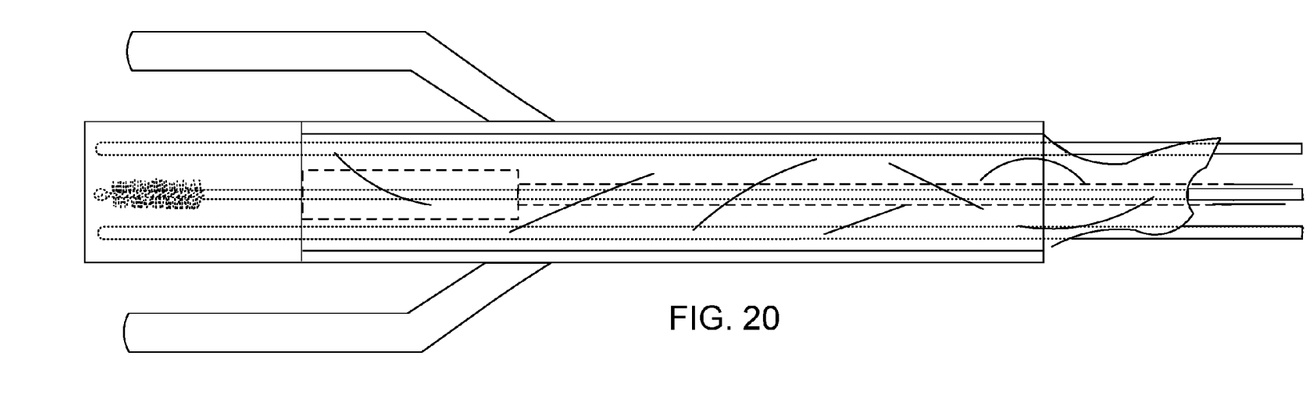

FIGS. 19-20 show expanding mechanism 400 for expanding the vaginal canal. Expanding mechanism 400 is connected to protective guide 1. FIG. 19 shows expanding mechanism in its streamlined, non-expanded mode for insertion into the vaginal canal. After insertion, expanding mechanism 400 is expanded so that it appears as shown in FIG. 20. This allows for a wide field of view in the vagina.

Figure 21:
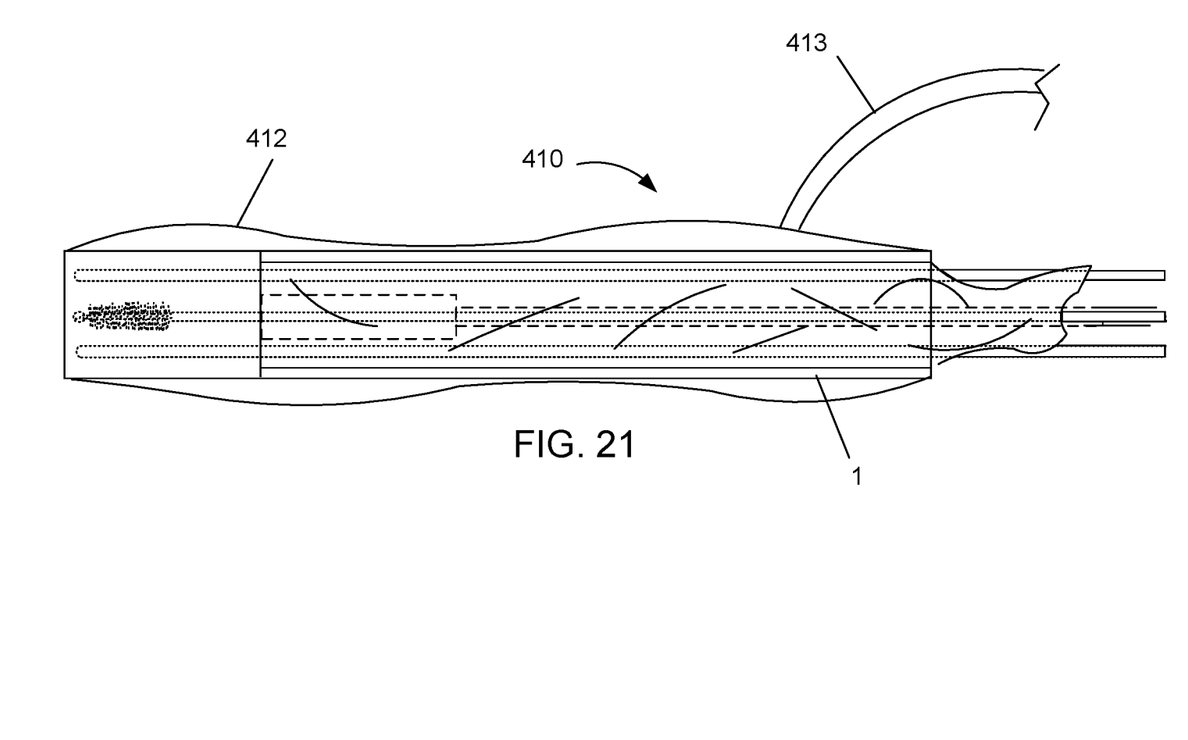
Figure 22:
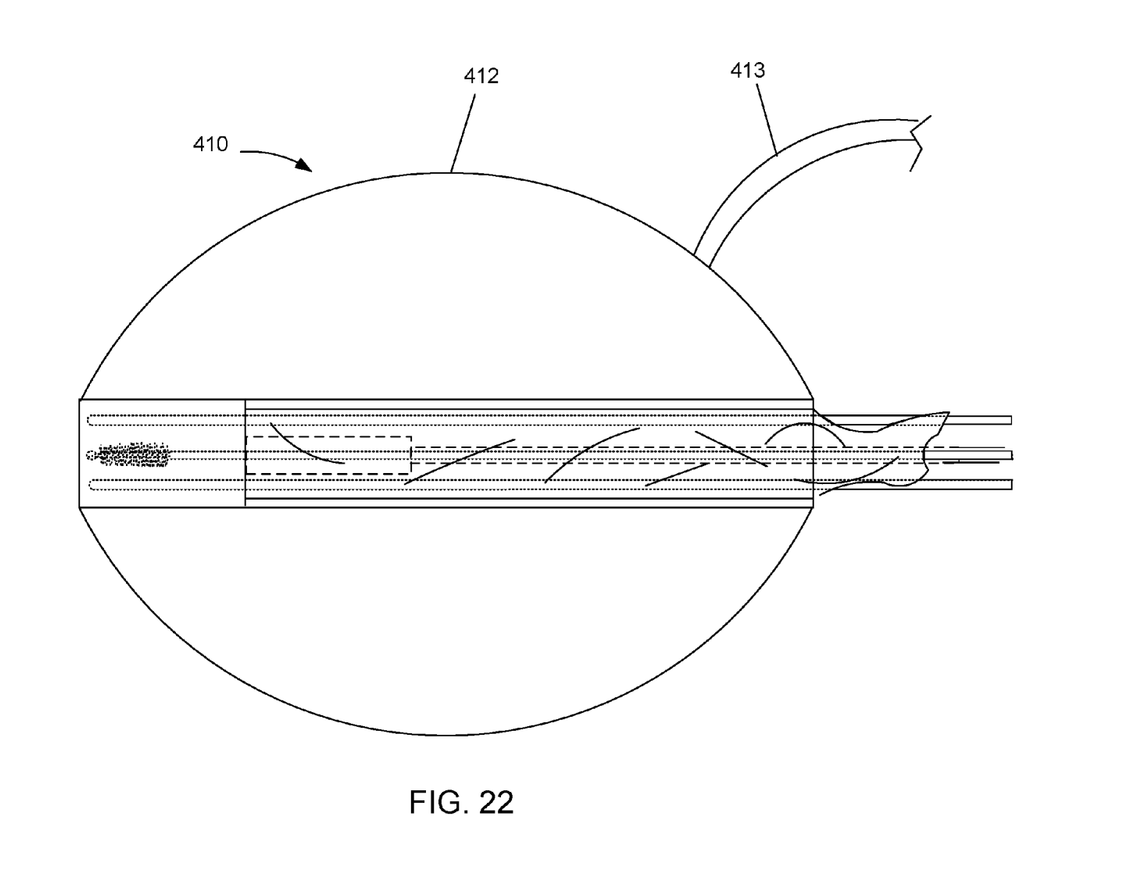

FIGS. 20-21 show expanding mechanism 410. Expanding mechanism 410 is an air filled ballooning mechanism surrounding protective guide 1. In FIG. 20, deflated balloon 412 is connected air fill tube 413 and is then inserted into the vaginal canal. After insertion, air is pumped into balloon 412 to expand expanding mechanism 410 (FIG. 22) to allow for a wider field of view in the vagina. When it is time to remove protective guide 1, air is sucked out of balloon 412 via fill tube 413 and protective guide 1 is removed.

Although the above-preferred embodiments have been described with specificity, persons skilled in this art will recognize that many changes to the specific embodiments disclosed above could be made without departing from the spirit of the invention. For example, even though the above preferred embodiments referred to the utilization of an endoscope and an endoscope cover, it should be understood that other types of cameras could also be substituted and the LEDS from the endoscope could also be replaced with other types of light emitting devices. Also, endoscope cover 6 may also be referred to as a camera cover. Likewise brush cover 2 and brush cover 201 may also be referred to as cell extraction device covers. Also, the above preferred embodiments discussed pap smear brush 2 extending outward from the rear of the protective guide 1 for hand control by a user. It should be recognized that the pap smear brush can be mechanically connected to a mechanical device that can control the extension, retraction and rotation of the pap smear brush. For example, in a preferred embodiment pap smear brush 2 is connected to a geared mechanism controlled by a knob. The user turns the knob to cause pap smear brush 2 to extend, retract and rotate. Also, in another preferred embodiment, in place of the pH probe described above, pH strips may be used in place of the pH probe to determine the hydrogen concentration of the vagina in different places. Therefore, the attached claims and their legal equivalents should determine the scope of the invention.

What is claimed is:

1. A protective guide for protecting a cell extraction device during a Pap smear, comprising:
   A. a camera,
   B. a light emitting device,
   C. a camera cover covering said camera and light emitting device,
   D. a thin flexible transparent sheath covering said camera cover, and
   E. a cell extraction device cover for covering said cell extraction device.

2. The protective guide as in claim 1, wherein said camera and light emitting device is an endoscope and said camera cover is an endoscope cover.

3. The protective guide as in claim 1, wherein said thin flexible transparent sheath is a condom covering said camera cover.

4. The protective guide as in claim 2, wherein said thin, flexible transparent sheath covers said endoscope cover, said endoscope and an endoscope cord.

5. The protective guide as in claim 1, wherein said cell extraction device cover comprises a tunnel and wherein said cell extraction device is inserted into said tunnel.

6. The protective guide as in claim 1, wherein said camera cover and said cell extraction device cover are press fit together.

7. The protective guide as in claim 1, further comprising at least one elastic band for holding said camera cover and said cell extraction device cover together.

8. The protective guide as in claim 1, wherein said cell extraction device is a Pap smear brush.

9. The protective guide as in claim 1, wherein said cell extraction device is a Pap smear broom.

10. The protective guide as in claim 1, wherein said cell extraction device is Pap smear spatula.

11. The protective guide as in claim 1, wherein the location of the cervix is determined by utilization of said camera, wherein said cell extraction device is pushed outward from said cell extraction device cover so that said cell extraction device head contacts the cervix and removes cells from the cervix, wherein said cell extraction device head is pulled back into said cell extraction device cover after said cells have been removed from the cervix.

12. The protective guide as in claim 1, further comprising a pH probe covered by said cell extraction device cover.

13. The protective guide as in claim 1, further comprising a temperature probe covered by said cell extraction device cover.

14. The protective guide as in claim 1 further comprising lighting rigidly mounted to said cell extraction device cover.

15. The protective guide as in claim 1, further comprising a fluid delivery tube covered by said cell extraction device cover.

16. The protective guide as in claim 1, further comprising a temperature probe connected to said protective guide.

17. The protective guide as in claim 1, further comprising a fluid delivery tube connected to said protective guide.

18. The protective guide as in claim 1 further comprising an expanding mechanism connected to said protective guide.

* * * * *